United States Patent
Cosmescu

(10) Patent No.: US 8,414,576 B2
(45) Date of Patent: Apr. 9, 2013

(54) SWIVEL DEVICE FOR ELECTROSURGERY PENCIL AND SURGICAL SMOKE EVACUATION

(76) Inventor: Ioan Cosmescu, Phoenix, AZ (US)

( * ) Notice: Subject to any disclaimer, the term of this patent is extended or adjusted under 35 U.S.C. 154(b) by 992 days.

(21) Appl. No.: 12/137,788

(22) Filed: Jun. 12, 2008

(65) Prior Publication Data

US 2009/0018539 A1  Jan. 15, 2009

Related U.S. Application Data

(63) Continuation-in-part of application No. 11/164,712, filed on Dec. 2, 2005.

(51) Int. Cl.
*A61B 18/18* (2006.01)
*A61B 18/04* (2006.01)

(52) U.S. Cl.
USPC ............... 606/41; 606/28; 606/32; 606/49

(58) Field of Classification Search ............ 604/19–22, 604/902, 27–52; 606/27–52
See application file for complete search history.

(56) References Cited

U.S. PATENT DOCUMENTS

| | | | |
|---|---|---|---|
| 3,582,114 A | 6/1971 | Andersen | |
| 3,906,955 A | 9/1975 | Roberts | |
| 4,152,017 A | 5/1979 | Abramson | |
| 4,541,802 A | 9/1985 | Olsen | |
| 4,676,241 A | 6/1987 | Webb et al. | |
| 4,719,914 A | 1/1988 | Johnson | |
| 4,850,352 A | 7/1989 | Johnson | |
| 4,907,582 A | 3/1990 | Meyerrose | |
| 4,919,129 A | 4/1990 | Weber, Jr. et al. | |
| 5,013,300 A * | 5/1991 | Williams | 604/119 |
| 5,055,100 A | 10/1991 | Olsen | |
| 5,062,420 A | 11/1991 | Levine | |
| 5,154,709 A | 10/1992 | Johnson | |
| 5,181,916 A | 1/1993 | Reynolds et al. | |
| 5,184,611 A | 2/1993 | Turnbull | |
| 5,192,267 A | 3/1993 | Shapira et al. | |
| 5,197,963 A | 3/1993 | Parins | |
| 5,259,376 A * | 11/1993 | Bales | 128/207.17 |
| 5,318,565 A | 6/1994 | Kuriloff et al. | |
| 5,325,851 A | 7/1994 | Reynolds et al. | |
| 5,360,427 A | 11/1994 | Majlessi | |
| 5,413,575 A | 5/1995 | Haenggi | |
| 5,435,306 A | 7/1995 | Stuart | |
| 5,496,314 A | 3/1996 | Eggers | |
| 5,507,535 A | 4/1996 | McKamey et al. | |
| 5,522,825 A | 6/1996 | Kropf et al. | |
| 5,897,417 A | 4/1999 | Grey | |
| 5,951,548 A * | 9/1999 | DeSisto et al. | 606/42 |
| 6,189,408 B1 | 2/2001 | Scheidling et al. | |
| 6,524,307 B1 | 2/2003 | Palmerton et al. | |
| 6,932,390 B1 | 8/2005 | Gretz | |
| 7,188,623 B2 | 3/2007 | Anderson et al. | |
| 2002/0019631 A1 * | 2/2002 | Kidder et al. | 606/42 |
| 2007/0129722 A1 | 6/2007 | Cosmescu | |

FOREIGN PATENT DOCUMENTS

WO  97/14364 A1  4/1997

* cited by examiner

*Primary Examiner* — Nicholas Lucchesi
*Assistant Examiner* — Leah Stohr
(74) *Attorney, Agent, or Firm* — Zeman—Mullen & Ford, LLP

(57) ABSTRACT

A swivel device for connection to an ESU pencil, an exhaust port of an ESU pencil with an integrated smoke evacuation system, or an exhaust port of an ESU pencil smoke evacuation shroud attachment includes a fixed member attached to a rotating member. The rotating member allows an electrical cord and/or vacuum tube to twist and coil freely during operation of an ESU pencil with or without the smoke evacuation system.

18 Claims, 4 Drawing Sheets

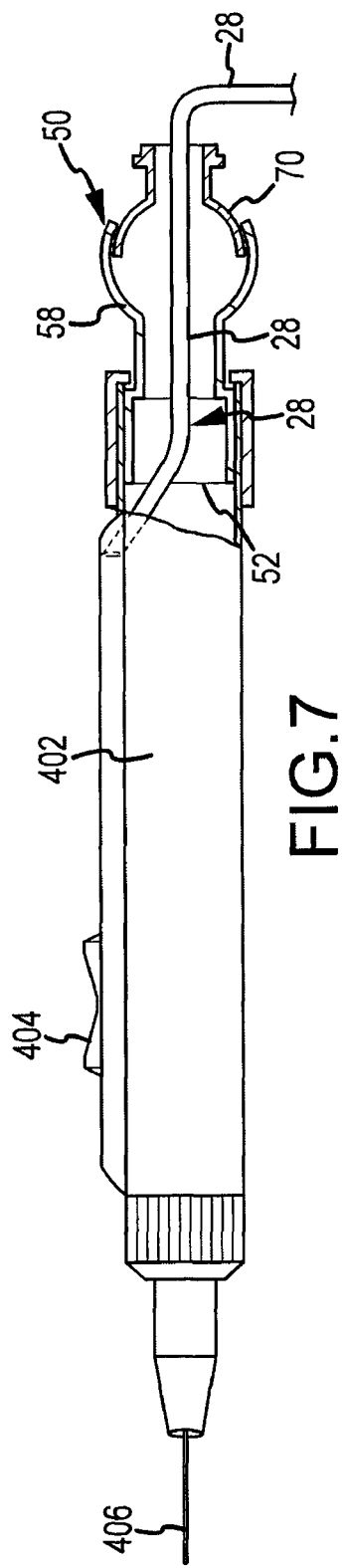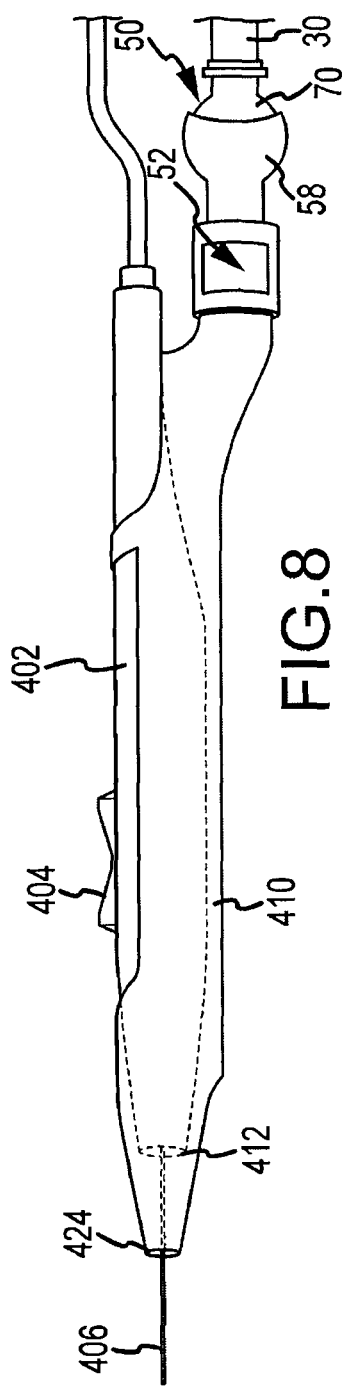

SWIVEL DEVICE FOR ELECTROSURGERY PENCIL AND SURGICAL SMOKE EVACUATION

CROSS-REFERENCE TO RELATED APPLICATIONS

This application is a continuation-in-part of currently pending application having Ser. No. 11/164,712, filed Dec. 2, 2005 which is herein incorporated in its entirety.

FIELD OF INVENTION

The present invention relates generally to a swivel apparatus. More specifically, the present invention relates to a swivel apparatus for attachment to or incorporation with the smoke evacuation system of an electro-surgical unit (ESU) pencil, and methods for making the same. The invention also relates to a swivel apparatus that can be incorporated into the connection between an ESU pencil and the electrical cord of the ESU pencil where the ESU pencil may be used either with or without smoke evacuation.

BACKGROUND OF THE INVENTION

The use of ESU pencils for cutting tissue and coagulating blood vessels in surgical procedures is well known. When an ESU pencil is used for cutting or coagulation, smoke is produced. In the past, when a surgeon wanted to evacuate this smoke from the surgical field, the surgeon or an assistant had to hold a plastic suction wand, connected to vacuum tubing, near the site of smoke production. This became cumbersome in many surgical procedures, because two hands were required—one operating the ESU pencil and the other holding the suction device—and because the suction wand often obscured the surgeon's view of the surgical field. Therefore, smoke evacuation devices were developed which were either incorporated directly into the design of an ESU pencil or were attachable to an ESU pencil.

Built-in or attachable smoke evacuation devices have also proved problematic, however. Like the suction wand, these devices must be connected to a vacuum source via a vacuum tube. The vacuum tubing generally used is stiff, corrugated, rubber tubing. Due to its stiffness, the tubing often coils in such a way that it twists the ESU pencil in the hand of the surgeon and pulls down the other end of the ESU pencil. This pulling and twisting of the ESU pencil is problematic in delicate surgical procedures and often requires the surgeon to stop frequently to uncoil the tubing. Therefore, more flexible vacuum tubing has been tried. However, this tubing is either too soft, so that it collapses under suction, or too narrow, so that it obstructs airflow. These various problems with vacuum tubing have led many surgeons to not use built-in or attached smoke evacuation devices on ESU pencils. But the only alternative is the separate suction wand, which is often too cumbersome or visually obstructing. A separate suction wand also requires a second person to hold it on site which many times interferes with the work of the surgeon.

Therefore, a need exists for an improved connection between an ESU pencil's built-in or attached smoke evacuation system and a vacuum tube. Such a connection would allow the vacuum tube to twist and/or swivel without turning the ESU pencil in the surgeon's hand. The vacuum tube may twist in a clockwise and/or counterclockwise direction. This improved connection would reduce the drag (or pulling down of) the distal end of the ESU pencil (i.e. that end of the ESU pencil opposite the electrode). In addition, the vacuum tube may also pivot in vertical up and down directions. The connection would also remain airtight, so that the force of the smoke evacuation system's vacuum is not reduced.

A need also exists for an improved connection between an ESU pencil and the electrical cord attached to the ESU pencil that allows the electrical cord to twist thereby facilitating a surgeon's use of the ESU pencil by reducing the drag or pulling down of the distal end of the ESU pencil (i.e. that end of the ESU pencil opposite the electrode).

SUMMARY OF THE INVENTION

The present invention is directed to a swivel device which includes a fixed member which can be attached to at least one of an outer body of an ESU pencil, an exhaust port of an ESU pencil with an integrated smoke evacuation system, or an exhaust port of an ESU pencil smoke evacuation shroud attachment, and a rotating member having a first end, a second end, and an angled portion located between the first and second ends. The first end of the rotating member is coupled to an interior of the fixed member. The angled portion of the rotating member may form approximately a 45 degree angle.

In one aspect of the invention, the fixed member and rotating member may be hollow tubular members each having first and second ends where the second end of the fixed member fits precisely around the first end of the rotating member thereby allowing rotation of the rotating member within the fixed member. In order to perform smoke evacuation, the second end of the rotating member is coupled to a vacuum tube such that the rotating member forms a leak proof connection with the vacuum tube. The rotating member preferably has a smooth interior cylindrical surface for conducting smoke and debris to the vacuum tube.

In one exemplary embodiment of the invention, the fixed member is capable of removable attachment to an outer body of an ESU pencil, an exhaust port of an ESU pencil with an integrated smoke evacuation system, and an exhaust port of an ESU pencil smoke evacuation shroud attachment.

In another exemplary embodiment, at least a portion of an electrical cord for providing power to the ESU pencil is contained within the fixed member and the rotating member. In addition, smoke evacuation may or may not also occur through the fixed member and the rotating member.

Yet another exemplary embodiment of the swivel device of the present invention includes a fixed member attached to an outer body of an ESU pencil, an exhaust port of an ESU pencil with an integrated smoke evacuation system, or an exhaust port of an ESU pencil smoke evacuation shroud attachment, a rotating member with first and second ends where the first end is coupled to an interior of the fixed member and the second end has a cup like shape, and a pivoting member having first and second ends where the first end includes a cup like shape and is coupled to an interior of the second end of the rotating member. Like the above described exemplary embodiments, the fixed member may be capable of removable attachment to an outer body of an ESU pencil, an exhaust port of an ESU pencil with an integrated smoke evacuation system, or an exhaust port of an ESU pencil smoke evacuation shroud attachment. The fixed member, rotating member, and pivoting member may all be hollow and each include first and second ends such that the second end of the fixed member fits precisely around the first end of the rotating member to allow rotation of the rotating member within the fixed member and the second end of the rotating member fits precisely within the first end of the pivoting member to allow the pivoting member to pivot in at least a vertical up and down direction.

BRIEF DESCRIPTION OF THE DRAWINGS

A more complete understanding of the present invention may be derived by referring to the detailed description and claims when considered in connection with the following illustrative figures, which may not be to scale. In the following figures, like reference numbers refer to similar elements throughout the figures.

FIG. 7 is a side view of an ESU pencil with an electrical cord for powering the ESU pencil permanently incorporated in the swivel device shown in FIGS. 5-6 with the electrical cord shown in phantom.

FIG. 8 is a perspective view of an ESU pencil with a smoke evacuation shroud attachment shown connected to the swivel device shown in FIGS. 5-6.

DETAILED DESCRIPTION

Figure 1:
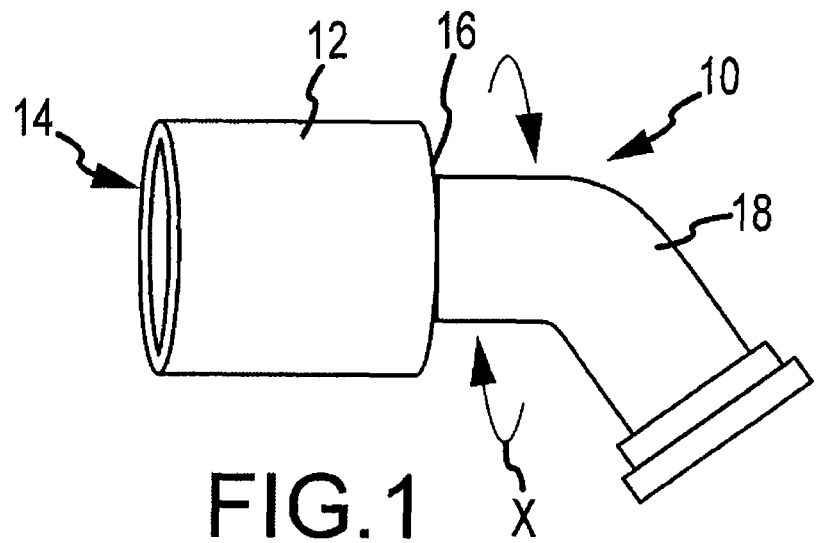
FIG. 1 is a perspective view of one exemplary embodiment of a swivel device according to the present invention, for attachment to an outer body of an ESU pencil, an exhaust port of an ESU pencil with an integrated smoke evacuation system, or an exhaust port of an ESU pencil smoke evacuation shroud attachment.
Figure 2:
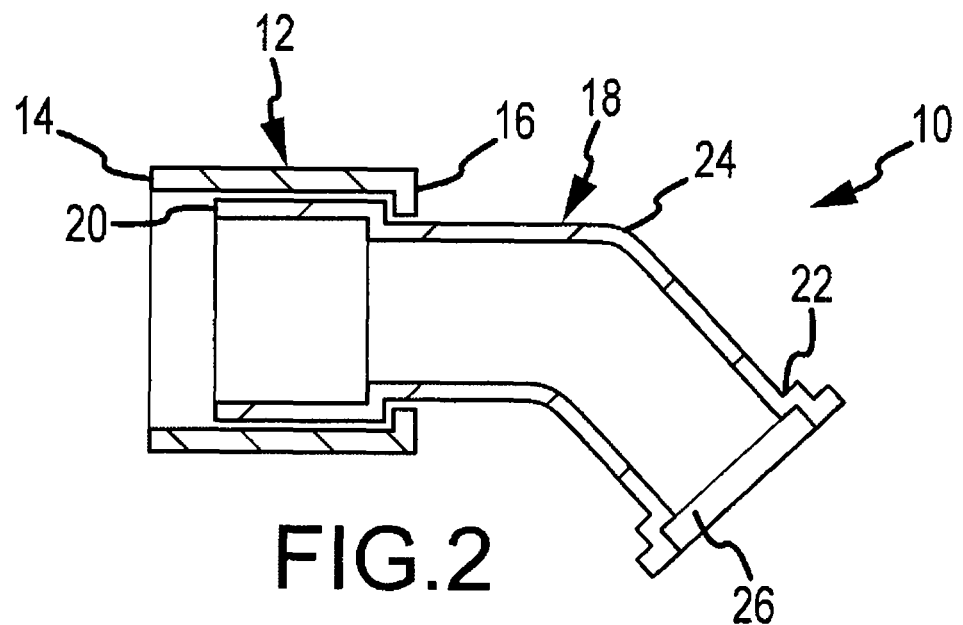
FIG. 2 is a cross-sectional view of the swivel device in FIG. 1.

One exemplary embodiment of the swivel device 10 of the present invention is shown in FIG. 1. Swivel device 10 includes a fixed member 12 having a first end 14 and a second end 16, and rotating member 18 which is coupled to an interior of the fixed member 12. Rotating member 18 includes a first end 20 (see FIG. 2), a second end 22, and an angled portion 24 located between first end 20 and second end 22. Second end 22 of rotating member 18 may further include a collar 26 which is capable of forming a leak proof connection with a vacuum tube (see FIG. 4).

Fixed member 12 and rotating member 18 may comprise hollow tubular members with smooth interior cylindrical surfaces which facilitate evacuation of smoke from a surgical site through a vacuum tube. Second end 16 of fixed member 12 is friction fit around first end 20 of rotating member 18 thereby allowing rotation of rotating member 18 within fixed member 12 as indicated by arrow X. The rotating member 18 may rotate in both clockwise and counterclockwise directions. This rotation of rotating member 18 which is connected to a vacuum tube (see FIG. 4) reduces the drag (or pulling down of) the distal end of the ESU pencil (i.e., the end of the ESU pencil opposite the electrode).

Fixed member 12 and rotating member 18 of swivel device 10 are preferably made of a sturdy and durable material which enables the friction fit of rotating member 18 within fixed member 12 while still allowing for the rotation of rotating member 18 within fixed member 12. Examples of such materials include, but are not limited to, polymers, plastics, fiberglass, etc.

Figure 3:
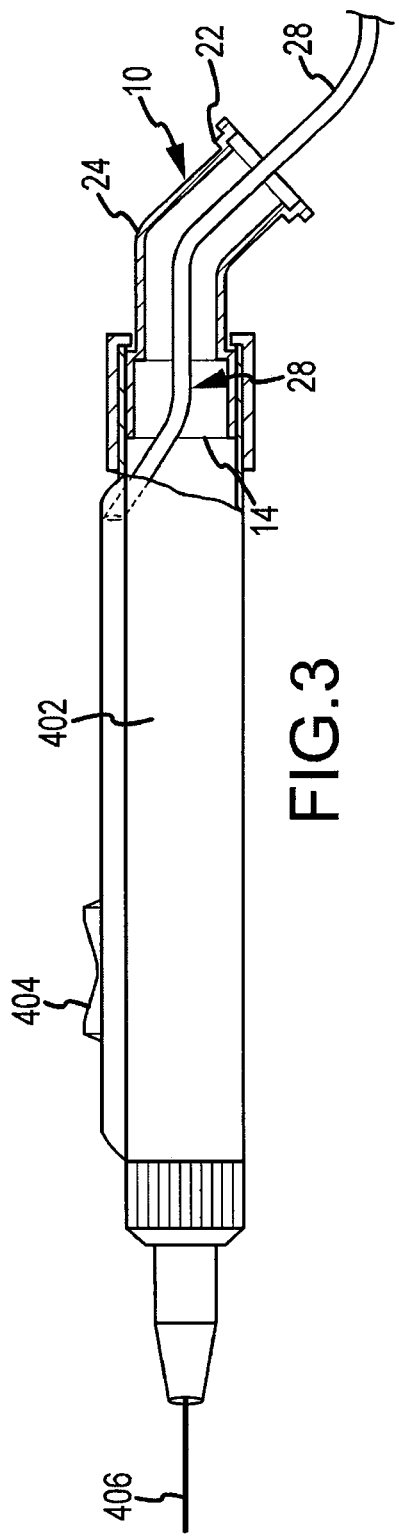
FIG. 3 is a side view of an ESU pencil with an electrical cord for powering the ESU pencil permanently incorporated in the swivel device shown in FIGS. 1-2 with the electrical cord shown in phantom.

A side view of an ESU pencil 402 with an electrical cord for powering the ESU pencil 402 permanently incorporated in swivel device 10 with the electrical cord 28 shown in phantom is depicted in FIG. 3. Electrical cord 28 is routed through swivel device 10 so that electrical cord 28 does not twist the ESU pencil in the hand of the surgeon during an electrosurgery procedure. In another exemplary embodiment, ESU pencil 402 may comprise a telescopic ESU pencil as shown in FIG. 3 which may accommodate smoke evacuation through its interior. In the event that smoke evacuation is accommodated through an interior of ESU pencil 402, swivel device 10 may also be coupled to a vacuum tube as shown in FIG. 4 to evacuate smoke from the surgical site.

Figure 4:
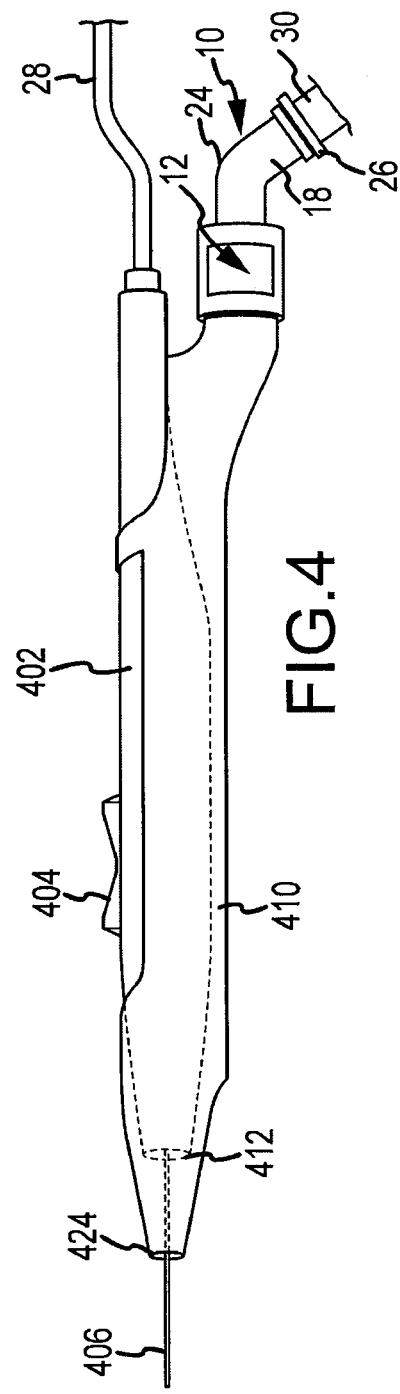
FIG. 4 is a perspective view of an ESU pencil with a smoke evacuation shroud attachment shown connected to the swivel device shown in FIGS. 1-2.

FIG. 4 shows a perspective view of an ESU pencil 402 with a smoke evacuation shroud attachment 410 shown connected to swivel device 10 of the present invention. Collar 26 of rotating member 18 fits over vacuum tube 30 to create an airtight connection between vacuum tube 30 and rotating member 18. Alternatively, second end 22 of rotating member 18 may be tapered to fit inside of vacuum tube 30, also creating an airtight connection between rotating member 18 and vacuum tube 30. Like the connection of swivel device 10 with ESU pencil 402 shown in FIG. 3, the connection between swivel device 10 and smoke evacuation shroud attachment 410 reduces the drag, or pulling down of, the distal end of the smoke evacuation shroud attachment 410 while the surgeon performs an electrosurgery procedure.

Figure 5:
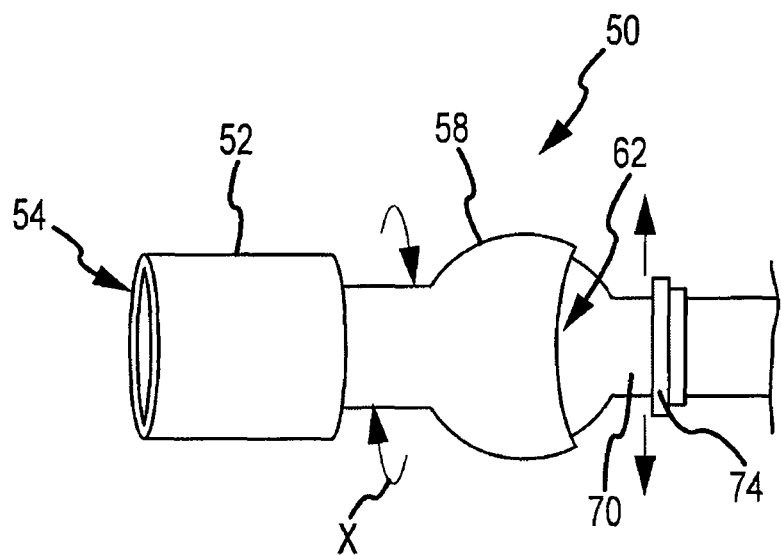
FIG. 5 is another exemplary embodiment of a swivel device according to the present invention, for attachment to an outer body of an ESU pencil, an exhaust port of an ESU pencil with an integrated smoke evacuation system, or an exhaust port of an ESU pencil smoke evacuation shroud attachment.
Figure 6:
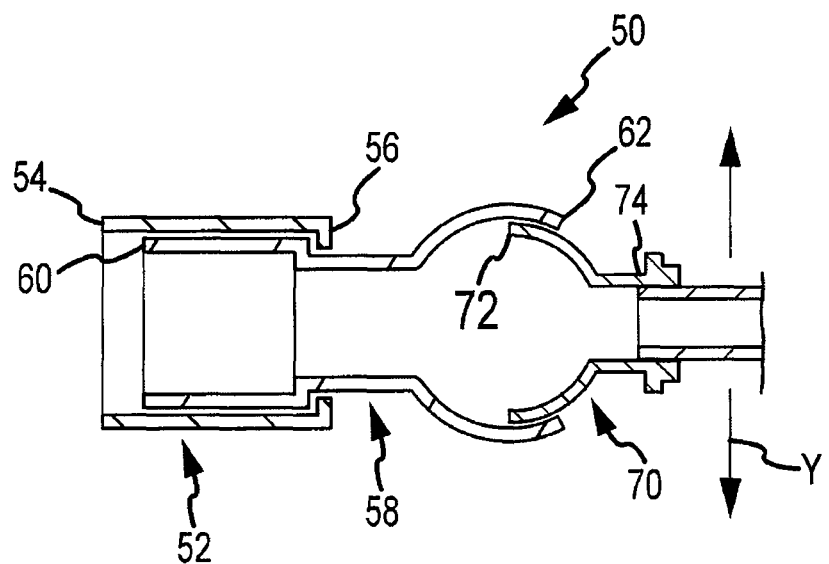
FIG. 6 is a cross-sectional view of the swivel device shown in FIG. 5.

Another exemplary embodiment of swivel device 50 in accordance with the present invention is shown in FIGS. 5-6. Swivel device 50 may be attached to an outer body of an ESU pencil, an exhaust port of an ESU pencil with an integrated smoke evacuation system, or an exhaust port of an ESU pencil smoke evacuation shroud attachment. Swivel device 50 includes a fixed member 52 having a first end 54 and second end 56, a rotating member 58 having a first end 60 and a second end 62, and a pivoting member 70 having a first end 72 and second end 74. Second end 56 of fixed member 52 is friction fit around first end 60 of rotating member 58 such that rotating member 58 is capable of rotating within fixed member 52. Second end 62 of rotating member 58 comprises an open-ended hollow half sphere shape, or cup like shape. In addition, first end 72 of pivoting member 70 also comprises an open-ended hollow half sphere shape, or cup like shape, which is friction fit within an interior of the cup like shape of first end 60 of rotating member 58 thereby allowing pivoting member 70 to pivot within rotating member 58 at least in a vertical up and down direction as indicated by arrow Y. In addition, pivoting member 70 may also pivot in a number of different directions relative to second end 62 of rotating member 58. This exemplary embodiment of swivel device 10 of the present invention provides a broader range of motion for the movement of a vacuum tube 30 or electrical cord 28 with respect to an ESU pencil 402 or smoke evacuation shroud attachment 410 to further decrease drag on the distal end of the ESU pencil or smoke evacuation shroud attachment 410 and to reduce twisting of vacuum tube 30 and/or electrical cord 28 while a surgeon performs an electrosurgery procedure.

With respect to the exemplary embodiment of swivel device 50 shown in FIGS. 5-6, the present invention also contemplates a swivel device which includes only rotary member 58 and pivoting member 70 whereby first end 60 of rotating member 58 would be attached in a leak proof manner to an outer body of an ESU pencil, and exhaust port of an ESU pencil with an integrated smoke evacuation system, or a exhaust port of an ESU pencil smoke evacuation shroud attachment. The connection between second end 62 of rotating member 58 and first end 72 of pivoting member 70 would then provide the sole means for vacuum tube 30 and/or electrical cord 28 to swivel, rotate, and/or pivot in relation to ESU pencil 402 or ESU pencil smoke evacuation shroud attachment 410.

FIG. 7 is a side view of an ESU pencil with an electrical cord for powering the ESU pencil permanently incorporated in swivel device 50 shown in FIGS. 5-6 with electrical cord 28 shown in phantom. Electrical cord 28 is routed through swivel device 50 so that electrical cord 28 does not twist the ESU pencil in the hand of the surgeon during an electrosurgery procedure. In another exemplary embodiment, ESU pencil 402 may comprise a telescopic ESU pencil as shown in FIG. 7 which may accommodate smoke evacuation through its interior. In the event that smoke evacuation is accommodated through an interior of ESU pencil 402, swivel device 50 may also be coupled to a vacuum tube as shown in FIG. 8 to evacuate smoke from the surgical site.

A perspective view of an ESU pencil with a smoke evacuation shroud attachment shown connected to swivel device 50 is shown in FIG. 8. Second end 74 of pivoting member 70 is coupled to vacuum tube 30 to create an airtight connection between vacuum tube 30 and pivoting member 70. Second end 74 of rotating member 70 may be tapered to fit inside of vacuum tube 30. Like the connection of swivel device 50 with ESU pencil 402 shown in FIG. 7, the connection between swivel device 50 and smoke evacuation shroud attachment 410 reduces the drag, or pulling down of, the distal end of the smoke evacuation shroud attachment 410 while the surgeon performs an electrosurgery procedure.

Operation

Referring to FIG. 4, before beginning a surgical procedure, the second end 22 of rotating member 18 is connected to the vacuum tube 30 which is connected to a vacuum source (not shown) and the power cord 28 for the ESU pencil 402 is connected to a power source (not shown). When desired, the surgeon then uses hand switch 404 to send radio frequency energy to the ESU pencil's 402 electrode 406, for cutting and coagulation. When the vacuum source is activated, smoke and debris from cutting and coagulation are sucked into the exhaust opening 424 at the distal end of nozzle 412 of the ESU pencil's 402 smoke evacuation shroud attachment 410. The smoke and debris then travel through the smoke evacuation shroud attachment 410, swivel device 10, and vacuum tube 30, to a vacuum canister (not shown). The operation of the ESU pencil 402 with smoke evacuation shroud attachment 410 is described in full detail in U.S. Pat. Nos. 5,836,944, 6,099,525, and 6,124,995.

It will be understood by one skilled in the art that second end 16 of fixed member 12 and first end 20 of rotating member 18 may take the form of alternative configurations and shapes to enable an airtight seal between fixed member 12 and rotating member 18. For example, second end 16 of fixed member 12 may take the shape and form of a larger outer-diameter portion of the fixed member as described in U.S. patent application having Ser. No. 11/164,712, filed Dec. 2, 2005. In addition, first end 20 of rotating member 18 may include an inverted distal end on the interior surface of the rotating member and a central inversion on the exterior surface of the rotating member as previously described in detail in U.S. patent application having Ser. No. 11/164,712, filed Dec. 2, 2005.

The present invention has been described above with reference to exemplary embodiments. However, those skilled in the art, having read this disclosure, will recognize that changes and modifications may be made to the exemplary embodiments without departing from the scope of the present invention. For example, the swivel device of the present invention may also be used or incorporated with laser or fiber optic surgical pencils that are employed along with suction devices to eliminate smoke and debris from the surgical site. These and other changes or modifications are intended to be included within the scope of the present invention, as expressed in the following claims.

The invention claimed is:

1. A swivel device comprising:
 a fixed member attached to at least one of an ESU pencil and an exhaust port of an ESU pencil with an integrated smoke evacuation system; and
 a rotating member having a first end, a second end, and an angled portion located between the first and second ends wherein the first end is coupled to an interior of the fixed member and at least a portion of an electrical cord for providing power to said ESU pencil or said ESU pencil with an integrated smoke evacuation system is contained within the fixed member and the rotating member.

2. The apparatus of claim 1 wherein the angled portion of the rotating member comprises approximately a forty five degree angle.

3. The apparatus of claim 1 wherein the fixed member comprises a hollow tubular member having a first end and a second end.

4. The apparatus of claim 3 wherein the rotating member comprises a hollow tubular member and the second end of the fixed member fits precisely around the first end of the rotating member thereby allowing rotation of the rotating member within the fixed member.

5. The apparatus of claim 1 wherein the second end of the rotating member is capable of forming a leak proof connection with a vacuum tube.

6. The apparatus of claim 5 wherein the rotating member has a smooth interior cylindrical surface for conducting smoke and debris to the vacuum tube.

7. The device of claim 1 wherein said fixed member is capable of removable attachment to at least one of said ESU pencil and said exhaust port of an ESU pencil with an integrated smoke evacuation system.

8. A swivel device comprising:
 a fixed member attached to at least one of a group consisting of an outer body of an ESU pencil, an exhaust port of an ESU pencil with an integrated smoke evacuation system, and an exhaust port of an ESU pencil smoke evacuation shroud attachment;
 a rotating member having a first end and a second end wherein the first end is coupled to an interior of the fixed member and the second end comprises a cup like shape; and
 a pivoting member having a first end and a second end wherein the first end comprises a cup like shape and is coupled to an interior of the second end of the rotating member.

9. The apparatus of claim 8 wherein the rotating member comprises a hollow tubular member and the second end of the fixed member fits precisely around the first end of the rotating member thereby allowing rotation of the rotating member within the fixed member.

10. The apparatus of claim 9 wherein the pivoting member comprises a hollow tubular member and the second end of the rotating member fits precisely within the first end of the pivoting member thereby allowing the pivoting member to pivot in at least a vertical up and down direction.

11. The apparatus of claim 10 wherein the rotating member and the pivoting member each have a smooth interior cylindrical surface for conducting smoke and debris to the vacuum tube.

12. The apparatus of claim 8 wherein the second end of the pivoting member is capable of forming a leak proof connection with a vacuum tube.

13. The device of claim 8 wherein said fixed member is capable of removable attachment to at least one of the group consisting of an outer body of an ESU pencil, an exhaust port of an ESU pencil with an integrated smoke evacuation system, and an exhaust port of an ESU pencil smoke evacuation shroud attachment.

14. The device of claim 8 wherein at least a portion of an electrical cord for providing power to the ESU pencil is contained within the fixed member and the rotating member.

15. A method for making a swivel device comprising the steps of:
proviing a fixed hollow member having a first end and a second end wherein the first end is capable of attachment to at least one of an ESU pencil and an exhaust port of an ESU pencil with an integrated smoke evacuation system;
providing a rotating hollow member having a first end and a second end;
coupling the first end of the rotating hollow member to an interior surface of the second end of the fixed hollow member;
providing a pivoting member having a first end and a second end; and
coupling the first end of the pivoting member to an interior of the second end of the rotating member.

16. The method of claim 15 wherein the step of providing a rotating hollow member comprises providing a rotating hollow member having a first end and a second end wherein the second end of the rotating member is capable of forming a leak proof connection with a vacuum tube.

17. The method of claim 15 wherein the second end of the rotating member and the first end of the pivoting member each comprise a cup like shape wherein the second end of the rotating member fits precisely within the first end of the pivoting member thereby allowing the pivoting member to pivot in at least a vertical up and down direction.

18. A method for making a swivel-based surgical pencil comprising the steps of:
attaching a first end of a fixed member to at least one of an outer body of an ESU pencil and an exhaust port of an ESU pencil with an integrated smoke evacuation system; and
coupling a first end of a rotating member to an interior surface of a second end of the fixed member such that at least a portion of an electrical cord for providing power to said ESU pencil or said ESU pencil with an integrated smoke evacuation system is contained within the fixed member and the rotating member.

* * * * *